United States Patent [19]

Jones et al.

[11] Patent Number: 4,591,648
[45] Date of Patent: May 27, 1986

[54] HISTIDINE PROTECTION

[75] Inventors: John H. Jones, Oxford; Tom Brown, Cambridge, both of England

[73] Assignee: National Research Development Corp., London, England

[21] Appl. No.: 361,432

[22] Filed: Mar. 24, 1982

[30] Foreign Application Priority Data

Apr. 1, 1981 [GB] United Kingdom ............... 8110116

[51] Int. Cl.$^4$ .......................................... C07D 233/64
[52] U.S. Cl. .................................................. 548/344
[58] Field of Search ............... 424/177; 260/112.5 R; 548/344

[56] References Cited

U.S. PATENT DOCUMENTS 3,821,188 6/1974 McKinley et al. ............ 424/112.5 R
4,100,152 7/1978 Fujino et al. .................... 424/177

FOREIGN PATENT DOCUMENTS 2449167 4/1976 Fed. Rep. of Germany .

OTHER PUBLICATIONS

Protection of Histidine Side-Chains with π-Benzyloxymethyl- or π-Bromobenzyloxymethyl-Groups, by Tom Brown and John Jones, JCS Chem. Comm. 1981, 648.

Journal of the Chemical Society, Chemical Communications, 1978, "An Approach to the Prevention of Racemisation in the Synthesis of Histidine-Containing Peptides, by John H. Jones and William I. Ramage; p. 473.

The Use of the N(π)-Phenacyl Group for the Protection of Histidine Side Chain in Peptide Synthesis, JCS 1979, by Andrew R. Fletcher, John Jones et al.

Racemisation and Protection in the Synthesis of Histidine Peptides by Andrew R. Fletcher, John H. Jones et al., Peptides 1978-Wroclaw University Press, Poland 1979, pp. 170-171.

A Protecting Group for the Pyrrole Nitrogen by H. J. Anderson and J. K. Groves, Tetrahedron Letters No. 34, p. 3165.

Jones et al., J. Chem. Soc., Perkin Trans. I, 1553-61 (1982).

CAS Registry Handbook 79950-65-5 and 79950-66-6.

Peptide Hormones, edited by Parsons, University Park Press, Baltimore, 1976, pp. 1-7.

Primary Examiner—Delbert R. Phillips
Assistant Examiner—F. T. Moezie
Attorney, Agent, or Firm—Oblon, Fisher, Spivak, McClelland & Maier

[57] ABSTRACT

Histidine derivatives of formula I are useful inter alia in peptide synthesis.

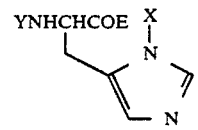

wherein:
X represents —CH$_2$OCH$_2$Ar, in which Ar is a phenyl substituent optionally substituted by one or more halogen, alkoxy, alkyl or nitro groups;
Y, which differs from X, represents hydrogen, a protective group capable of inhibiting self coupling during formation of a peptide bond, an amino acid residue, a peptide chain or an antibiotic residue;
E represents OH,OM,M representing an alkali metal or ammonium, OR, R representing an alkyl, aryl, aralkyl or alkaryl group, an amino acid residue, a peptide chain or an antibiotic residue;
the compound I being optionally in the form of a hydrate or acid salt.

In compounds I of especial interest, X represents benzyloxymethyl or p-bromobenzyloxymethyl, Y represents t-butyloxycarbonyl and E represents —OH.

15 Claims, No Drawings

HISTIDINE PROTECTION

This invention relates to histidine derivatives useful in particular for the synthesis of peptides.

When differing amino acids are coupled together to form peptides it is generally necessary for an amino or carboxylic acid group on each molecule to be protected so that self-coupling does not take place. In histidine it has also usually be desirable to protect the side chain by substitution of the N-H group on the imidazole ring with benzyl, 2,4-dinitrophenyl, p-toluenesulphonyl, or t-butyloxycarbonyl groups. Problems have been encountered with all these protecting groups, however; some at least allow racemisation to occur on activation for coupling; all except the benzyl group show reactivity towards nucleophiles; the benzyl group is removable only under undesirably vigorous conditions; the solubility of the benzyl and 2,4-dinitrophenyl derivatives is in many cases undesirably low. Whilst racemisation can be avoided by the use of a $\pi$-phenacyl group, the complexity of such a group and the conditions required for its ultimate removal give rise to undesirable side reactions.

Intermediates useful in the synthesis inter alia of peptides comprising histidine have now been found which overcome at least some of the above problems.

Accordingly, the present invention comprises a compound of formula I:

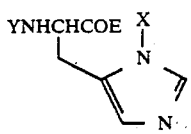

wherein:
X represents —CH$_2$OCH$_2$Ar, in which Ar is a phenyl substituent optionally substituted by one or more halogen, alkoxy (e.g. C$_1$–C$_6$ alkoxy), alkyl (e.g. C$_1$–C$_6$ alkyl) or nitro groups;

Y, which differs from X, represents hydrogen, a protective group capable of inhibiting self coupling during formation of a peptide bond, an amino acid residue, a peptide chain or an antibiotic residue;

E represents OH, OM, M representing an alkali metal or ammonium, OR, R representing an alkyl (e.g. an C$_1$–C$_6$ alkyl), aryl, alkaryl or aralkyl (e.g. a benzyl) group, an amino acid residue, a peptide chain or an antibiotic residue;

the compound I being optionally in the form of a hydrate or acid salt.

Compounds of formula I in which Ar in X represents phenyl, bromophenyl or chlorophenyl (e.g. p-bromophenyl or p-chlorophenyl) or 2,4,6-trimethylphenyl are of particular interest. The group X is usually readily removable when protection is no longer required in the case wherein Ar represents phenyl by, for example, hydrogenation using a catalyst such as palladium on carbon or by treatment with hydrogen bromide in acetic acid or in trifluoroacetic acid and in the case wherein Ar represents 2,4,6-trimethylphenyl by, for example treatment with trifluoroacetic acid.

Typical protective groups Y which are usually readily movable include t-butyloxycarbonyl (Boc), benzyloxycarbonyl and 9-fluorenylmethoxycarbonyl (Fmoc) of which Boc is generally preferred. Compounds I in which Y represents hydrogen, comprising either free amino groups or acid salt derivatives thereof, may be produced from compounds I in which Y represents protective groups such as Boc by treatment with a suitable acidic reagent such as trifluoroacetic acid followed by neutralisation when appropriate. Such compounds I may be used to change protection from one protective group Y to another by, for example, treatment with an appropriate chloride. Benzyloxycarbonyl chloride and 9-fluorenylmethoxycarbonyl chloride thus generate compounds I in which Y represents respectively benzyloxycarbonyl and Fmoc. Compounds I in which Y represents H are of course also useful for linkage to an amino acid or a peptide or antibiotic typically by formation of a peptide bond comprising histidyl N($\alpha$).

Such products may comprise protective and other groups, typically groups such as hereinbefore described protecting one or more amino groups in the amino acid, peptide chain or antibiotic residue from self coupling and other side reactions during any further synthetic steps.

Compounds I in which E represents —OH i.e. in the form of free acids are of particular interest as intermediates and may be produced from compounds Ia in which E represents OM, M being an alkali metal or ammonium, by pH adjustment and also by hydrolysis of compounds Ia in which E represents OR, R typically representing a C$_1$–C$_6$ alkyl or an aryl group, using for example an alkali metal hydroxide followed by neutralisation. It is highly preferred, moreover, especially when Y represents the protective group Boc or benzyloxycarbonyl, that compounds I in which E represents —OH are produced from acid salt forms such as hydrochlorides of compounds Ia in which E represents OR by hydrolysis using alkali for example, followed by neutralisation.

Compounds of formula Ia in which E represents OR, in addition to finding application in the production of compounds of formula I in which E represents OH, are useful for the production of acid salts of compounds of formula Ib in which Y represents hydrogen and E represents —OR, by treatment of compounds Ia in which Y represents a protective group such as Boc and E represents OR with an appropriate acid reagent e.g. trifluoroacetic acid. The compounds Ib themselves may be conveniently regenerated from their acid salts when required, by base neutralisation using e.g. triethylamine.

In compounds I wherein E represents an amino acid residue, peptide chain or an antibiotic residue, the residue or chain is usually linked to the histidyl moiety by a peptide bond comprising the carbonyl group of the group —COE. The or each residue may comprise one or more protective or other group, typically a group such as those hereinbefore described protecting one or more amino groups on the amino acid residue, peptide chain or antibiotic residue from self coupling during any further synthetic steps.

Compounds of formula Ia in which E represents OR and especially those in which Y represents a protective group such as Boc or benzyloxycarbonyl may be produced from compounds of formula II

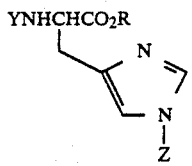

in which Z represents Boc or triphenylmethyl and Y is as in compounds Ia by a procedure in which the group X is introduced onto the π-nitrogen in the imidazole ring whilst the τ-nitrogen is temporarily blocked with the group Z. In this procedure a compound of formula II is preferably treated with a compound X-hal wherein hal represents halogen, preferably chlorine or bromine, typically in a suitable solvent such as diethyl ether or methylene dichloride and usually at ambient. When Z represents Boc, further treatment, if appropriate after removal of the solvent, with an alcohol, preferably methanol, or an alcohol in the presence of a base, preferably triethylamine gives a compound Ia in which E represents OR in the form of a salt or as the free base respectively. When Z represents triphenylmethyl, however, removal of Z may be accomplished by treatment of the product, generally after removal of the solvent, with a mildly acidic reagent, e.g. acetic acid, where appropriate in the presence of a halogen ion acceptor, e.g. a silver salt such as silver acetate, which removes halogen ion from solution to avoid the formation of strong acid which might attack the group X or be otherwise undesirable.

The present invention further includes within its scope compounds of formula II per se provided that when Y represents Boc and Z represents Boc or triphenylmethyl, R is other than a methyl group.

Compounds of formula I typically find application as intermediates in peptide synthesis by linkage, through reaction respectively, of free carboxylic acid and free amino groups, to amino acids and peptides which may carry protective and/or other groups. Such synthesis may be carried out classically or by solid phase techniques, by use of compounds I in which E generally represents —OH.

The invention is illustrated by the following Examples:

EXAMPLE 1

N(α)-t-Butyloxycarbonyl, N(π)-4-bromobenzyloxymethyl-L-histidine methyl ester

Method 1

4-Bromobenzyl bromomethyl ether (8.5 g, 30 mmol) is added dropwise to an ice-cooled solution of N(α)-t-butyloxycarbonyl, N(τ)-triphenylmethyl-L-histidine methyl ester (15.33 g, 30 mmol) in ether (100 ml). After 2 hours at ambient the supernatant is decanted to leave N(α)-t-butyloxycarbonyl, N(τ)-triphenylmethyl, N(π)-4-bromobenzyloxymethyl-L-histidine methyl ester imidazolium bromide as a gum (11 g) which is dissolved in 80% acetic acid (60 ml). Silver acetate (5 g, 30 mmol) is added and the mixture is stirred for 30 minutes, filtered and stirred at ambient overnight. Evaporation of the solvent affords an oil which is neutralised (saturated sodium bicarbonate) and extracted with ethyl acetate (5×50 ml). The combined ethyl acetate extracts are dried (anhydrous magnesium sulphate) and evaporated to a syrup (7.1 g). Flash silica-gel (230–400 mesh) column chromatography, eluting under slight pressure with chloroform: methanol (19:1) gives the methyl ester as a colourless oil (2.74 g, 19.5%) which solidifies when set aside at 4°; m.p. 108°. $[\alpha]_D^{20} -10.7°$ (c 1.03 in MeOH).

EXAMPLE 2

N(α)-t-Butyloxycarbonyl, N(π)-4-bromobenzyloxymethyl-L-histidinemethyl ester

Method 2

4-Bromobenzyl bromomethyl ether (0.9 g, 3 mmol) in ether (10 ml) is added to an ice-cooled solution of N(α), N(τ)-bis-t-butyloxycarbonyl-L-histidine methyl ester (1.1 g, 3 mmol) in ether (50 ml). The mixture is allowed to stand at ambient for 3 hours and evaporated. The residue is dissolved in methanol (15 ml) and triethylamine (1 ml) is added. Evaporation of the solvent affords a gum which is dissolved in methanol (15 ml) and set aside for 2 hours at ambient. The methanol is evaporated leaving a residue which is dissolved in ethyl acetate (25 ml): the solution is extracted with brine (3×20 ml), dried (anhydrous magnesium sulphate) and evaporated to a gum. Flash silica-gel (230–400 mesh) column chromatography, eluting with chloroform: methanol (19:1) gives the methyl ester (0.405 g, 28%), identical with that obtained in Example 1; m.p. 108°.

EXAMPLE 3

N(α)-t-Butyloxycarbonyl, N(π)-4-bromobenzyloxymethyl-L-histidine

A solution of the methyl ester (Examples 1 or 2) 2.74 g, 5.9 mmol) in methanol (12 ml) is treated with 1M sodium hydroxide (5.9 ml, 5.9 mmol). After 1 hour at ambient the solution is diluted with water (50 ml), acidified to pH 4 with 1M hydrochloric acid and extracted with dichloromethane (3×50 ml). The combined dichloromethane extracts are dried (anhydrous magnesium sulphate) and evaporated giving N(α)-t-butyloxycarbonyl, N(π)-4-bromobenzyloxymethyl-L-histidine (2.3 g, 86.5%) as a crisp white foam: m.p. 69°-74°, $[\alpha]_D^{20} -9.38°$ (c 1.0 in MeOH).

EXAMPLE 4

N(α)-t-Butyloxycarbonyl, N(π)-benzyloxymethyl-L-histidine methyl ester

Method 1

A solution of N(α), N(τ)-bis-t-butyloxycarbonyl-L-histidine methyl ester (1.85 g, 5 mmol) in dichloromethane (20 ml) is treated with benzyl chloromethyl ether (0.94 g, 6 mmol). The mixture is allowed to stand at ambient for 3 hours after which time evaporation of the solvent affords a residue which is dissolved in methanol (20 ml) and treated with triethylamine (1 ml). The solvent is removed by evaporation and the residue is dissolved in methanol (5 ml) and set aside at ambient for 2 hours. Evaporation of the solvent affords the crude methyl ester which is dissolved in ethyl acetate (25 ml), extracted with brine (3×25 ml) and dried (anhydrous magnesium sulphate). Purification by flash silica-gel (230–400 mesh) column chromatography, eluting under slight pressure with chloroform: methanol (19:1) gives the pure methyl ester (0.69 g, 35.4% which solidifies when triturated with 40°-60° petroleum ether: m.p. 103°, $[\alpha]_D^{20} -10.77°$ (c 0.55 in MeOH).

EXAMPLE 5

N(α)-t-Butyloxycarbonyl, N(π)-benzyloxymethyl-L-histidine methyl ester

Method 2

To a solution of N(α)-t-butyloxycarbonyl, N(τ)-triphenylmethyl-L-histindinemethyl ester (3.58 g, 7 mmol) in ether (20 ml) is added benzyl chloromethyl ether (1.21 g, 7.7 mmol). A crystalline product forms and the mixture is set aside at ambient overnight. The crystalline quaternary salt which separates (1.9 g, 41%) is then collected and washed several times with ether: m.p. 138°–141°, $[\alpha]_D^{20} -9.19°$ (c 0.56 in MeOH). To a solution of the quaternary salt (1.5 g, 2.25 mmol) in acetic acid (5 ml) is added silver acetate (0.38 g, 2.28 mmol). The mixture is stirred overnight at ambient, filtered and evaporated to a syrup. Saturated sodium bicarbonate (20 ml) is added to the residue and the mixture is extracted with ether (5×20 ml). The combined ether extracts are dried with anhydrous magnesium sulphate and purified by the chromatographic procedure described in Example 4. The pure methyl ester (0.49 g, 56%) is indistinguishable from that obtained in Example 4: m.p. 103°.

EXAMPLE 6

N(α)-t-Butyloxycarbonyl, N(π)-benzyloxymethyl-L-histidine

Method 1

A solution of the methyl ester (Examples 4 or 5) (1.25 g, 3.2 mmol) in methanol (10 ml) is treated with 1M sodium hydroxide (3.5 ml, 3.5 mmol). After 1 hour at ambient, water (50 ml) is added and the solution is acidifed to pH 5 by the addition of 1M hydrochloric acid. The solution is extracted with dichloromethane (3×30 ml) and the combined dichloromethane extracts are dried (anhydrous magnesium sulphate) and evaporated to a crisp foam (m.p. 68°–74°). Evaporation from ethyl acetate solution affords N(α)-t-butyloxycarbonyl-N(π)-benzyloxymethyl-L-histidine (0.95 g, 78.8%) as a solid, m.p. 155°, $[\alpha]_D^{20} +6.92°$ (c 0.54 in MeOH).

EXAMPLE 7

N(α)-t-Butyloxycarbonyl, N(π)-benzyloxymethyl-L-histidine methyl ester hydrochloride A solution of N(α), N(τ)-bis-t-butyloxycarbonyl-L-histidine methyl ester (32 g, 0.082 moles) and freshly redistilled benzyl chloromethyl ether (18 ml, 0.13 moles) in dichloromethane (200 ml) is set aside overnight. Evaporation of solvent, dissolution in methanol (30 ml), and addition of ether (400 ml) gives a slightly turbid solution from which protected ester hydrochloride (24 g, 69%) crystallises on standing overnight: m.p. 152° $[\alpha]_D^{20} -19.1°$ (c 1.0, MeOH).

EXAMPLE 8

N(α)-t-Butyloxycarbonyl, N(π)-benzyloxymethyl-L-histidine

Method 2

Sodium hydroxide (M, 120 ml) is added to a solution of the preceding ester hydrochloride (22 g, 0.052 moles) in methanol (50 ml). After 15 min water (1l) is added and the pH is adjusted to 4.5 by the dropwise addition of M hydrochloric acid. The solution is extracted with chloroform (3×100 ml) and the combined organic extracts are dried. Removal of the solvent gives an oil which is dissolved in ethyl acetate (50 ml). Evaporation gives acid (17 g, 87%) of m.p. 155°, $[\alpha]_D^{20} +6.9°$ (c 0.5, MeOH).

EXAMPLE 9

N(α)-Benzyloxycarbonyl-N(π)-4-bromobenzyloxymethyl-L-histidine

A solution of N(α)-t-butyloxycarbonyl-N(π)-4-bromobenzyloxymethyl-L-histidine (0.3 g, 0.63 mmol) in trifluoroacetic acid (5 ml) is set aside for 30 minutes at ambient. The trifluoroacetic acid is removed under reduced pressure and the residue is dissolved in dioxane (30 ml) which has been saturated with hydrogen chloride. The solvent is evaporated to leave an oil which is washed by decantation with ether (5×15 ml).

Excess ether is removed under reduced pressure to leave, as a glass, crude N(π)-4-bromobenzyloxymethyl-L-histidine dihydrochloride. A stirred solution of the foregoing amino acid hydrochloride (0.10 g, 0.234 mmol) in a mixture of 10% sodium carbonate (1 ml) and dioxane (0.75 ml) is treated with a solution of benzyl chloroformate (50 μL, ~0.3 mmol) in dioxane (1 ml). After 10 minutes a further aliquot of benzyl chloroformate (10 μL) in dioxane (0.5 ml) is added, and the reaction mixture is stirred for a further 30 minutes at ambient. Excess dioxane is removed under reduced pressure and water (25 ml) is added to the residue. The aqueous suspension is extracted with ether (10 ml), acidified to pH 4.5 by the addition of 1M hydrochloric acid and extracted with dichloromethane (5×15 ml). The combined dichloromethane extracts are dried (magnesium sulphate) and evaporated to an oil which is covered with ether (20 ml) and set aside at 4° overnight. Evaporation under reduced pressure leaves a glass.

Yield: 48 mgs, 42%, mpt 82°–85°; $[\alpha]_D^{20} -3.97°$ (c 0.53 in methanol)

EXAMPLE 10

N(α)-9-Fluorenylmethyloxycarbonyl-N(π)-benzyloxymethyl-L-histidine

A solution of N(α)-t-butyloxycarbonyl-N(π)-benzyloxymethyl-L-histidine (0.75 g, 2 mmol) in trifluoroacetic acid (5 ml) is set aside at ambient for 30 minutes, then evaporated to leave an oil, to which is added ether (50 ml). After 1 hour at ambient the ether is removed by decantation and the residue is dissolved in a mixture of 10% sodium carbonate (8 ml) and dioxane (8 ml). The mixture is stirred at 0° and a precipitate soon forms. To this mixture is added dropwise a solution of 9-fluorenylmethyl chloroformate (0.647 g, 2.5 mmol) in dioxane (2 ml). The mixture is set aside at ambient.

After 2 hours the pH of the solution is measured, and adjusted to pH 9 by the addition of 10% sodium carbonate. The volume is reduced to ca 10 ml under reduced pressure and then saturated potassium chloride (15 ml) and 10% aqueous citric acid (25 ml) are added. The aqueous solution is extracted with dichloromethane (5×15 ml) and the combined organic layers are dried (magnesium sulphate) and set aside at 4°. The crystalline product is collected and the mother liquors are treated with excess ether to give a precipitate which is also collected. The combined solids are dissolved in methanol (50 ml) and the methanol solution is reduced to 10 ml by evaporation. The solution is set aside at 4° overnight and the crystalline product is collected and washed with ether (5×10 ml).

Yield: 0.41 g, 41%, mpt 160° $[\alpha]_D^{20}+1.8°$ (c 0.56 in methanol).

EXAMPLE 11

SYNTHESIS OF THYROLIBERIN

N(α)-t-Butyloxycarbonyl, N(π)-4-bromobenzyloxymethyl-L-histidyl-L-prolineamide

To a solution of N(α)-t-butyloxycarbonyl, N(π)-(4-bromobenzyloxymethyl)-L-histidine monohydrate (0.236 g, 0.5 mmol) in DMF (5 ml), cooled to 0°, is added L-prolineamide hydrochloride (0.075 g, 0.05 mmol), triethylamine (0.071 ml, 0.05 mmol), 1-hydroxybenztriazole (0.077 g, 0.5 mmol) and N,N'-dicyclohexylcarbodi-imide (0.113 g, 0.55 mmol). The mixture is set aside at ambient overnight and the filtered solution is evaporated to a gum which is dissolved in dichloromethane (20 ml), extracted with 1M sodium bicarbonate (2×10 ml) and dried (anhydrous magnesium sulphate). Evaporation of the solvent affords a residue which is dissolved in dichloromethane (5 ml) and treated with 40° to 60° petroleum ether to incipient turbidity. The mixture is set aside at 4° overnight to crystallise. The crystalline dipeptide is recrystallised from dichloromethane-light petroleum: 0.19 g, 67%—m.p. 198° $[\alpha]_D^{20}-35.08°$ (c 0.5 in 1M acetic acid).

L-Pyroglutamyl-N(π)-4-bromobenzyloxymethyl-L-histidyl-L-prolineamide

The foregoing protected dipeptide (0.113 g, 0.2 mmol) is dissolved in trifluoroacetic acid (5 ml) and allowed to stand at ambient for 0.5 hours. Evaporation affords a solid which is washed several times with ether to leave N(π)-4-bromobenzyloxymethyl-L-histidyl-L-prolineamide, which is dissolved in DMF (5 ml) and adjusted to pH 9 by addition of triethylamine. L-Pyroglutamic acid trichlorophenyl ester (0.066 g, 0.21 mmol) is added and the mixture is set aside at ambient overnight. Evaporation of the solvent affords a residue which is washed with ether (3×10 ml) and applied to a Sephadex G15 column. Elution with 25% acetic acid and pooling of the major U.V. absorbing fraction gives the tripeptide. The chromatographic procedure is repeated to obtain the pure tripeptide as its hydrated acetate salt as an immobile gum which is dissolved in methanol (1 ml) and reprecipitated by the addition of ether (50 ml), to give an amorphous hygroscopic solid: (0.074 g, 66%), $[\alpha]_D^{20}-61.1°$ (c 1.0 in 1 M acetic acid), $[\alpha]_D^{20}-40.57°$ (c 0.525 in MeOH). Amino acid analysis Glu 1.0, His 0.99, Pro 0.98.

Thyroliberin

A solution of the foregoing protected tripeptide (0.03 g, 0.05 mmol) in methanol: acetic acid: water (8:1:1) is hydrogenated for 5 hours at atmospheric pressure in the presence of palladium on carbon catalyst (0.01 g, 10% Pd). The filtered solution is evaporated to leave a residue which is dissolved in 25% acetic acid and passed through a column of Amberlite IR45 ion-exchange resin (acetate form) to remove hydrogen bromide. Evaporation of the solvent affords a residue which is dissolved in methanol (1 ml) and added to ether (50 ml). The precipitated tripeptide (15.6 mgs, 65%) is collected by filtration to give the tripeptide, chromatographically indistinguishable from an authentic sample of thyroliberin, $[\alpha]_D^{20}-64.15°$ (c 0.41, in 1 M acetic acid) uncorrected for retained acetic acid and water. Amino acid analysis Glu 1.0, His 0.96, Pro 0.96.

EXAMPLE 12

GLYCYL-L-HISTIDYL-L-PHENYLALANINE

N(α-t-Butyloxycarbonyl-N(π)-4-bromobenzyloxymethyl-L-histidyl-L-phenylalanine 4-picolyl ester Solution I: A mixture of N(α)-t-butyloxycarbonyl, N(π)-4-bromobenzyloxymethyl-L-histidine (0.472 g, 1.02 mmol), 1-hydroxybenztriazole (0.155 g, 1.01 mmol) and N, N'-dicyclohexylcarbodiimide (0.226 g, 1.1 mmol) in DMF (5 ml) is set aside at 0° for 1 hour then at ambient for 1 hour.

Solution II: A solution of t-butyloxycarbonyl-L-phenylalanine 4-picolyl ester (0.356 g, 1.0 mmol) in trifluoroacetic acid (5 ml) is allowed to stand at ambient for 0.5 hours and is then evaporated to dryness and washed with ether (3×15 ml) which is removed by decantation. A solution of the residue in DMF (3 ml) is adjusted to pH 9 by the addition of triethylamine.

Solutions I and II are mixed and set aside overnight at ambient. The filtered solution is evaporated to dryness and the residue is dissolved in dichloromethane (25 ml), extracted with 1M sodium bicarbonate (2×15 ml) followed by water (15 ml) and then dried (anhydrous magnesium sulphate) and evaporated to an oil. A solution of the oil in ethyl acetate (25 ml) is extracted with citric acid (5×10 ml). The combined citric acid extracts are neutralised with solid sodium bicarbonate and extracted with ethyl acetate (5×15 ml). The combined ethyl acetate extracts are dried (anhydrous magnesium sulphate) and evaporated to an oil which is dissolved in ether (15 ml) and evaporated to a stable foam. The product is contaminated with a little N, N'-dicyclohexylurea but no purification is necessary at this state and the crude dipeptide (0.42 g, 50.7%) is used in subsequent reactions.

Benzyloxycarbonyl-glycyl-N(π)-4-bromobenzyloxymethyl-L-histidyl-L-phenylalanine 4-picolyl ester A solution of the foregoing protected dipeptide (0.41 g, 0.6 mmol) in trifluoroacetic acid (5 ml) is allowed to stand at ambient for 0.5 hours, evaporated and washed with ether (3×15 ml). The ether is removed by decantation to leave a residue which is dissolved in DMF (3 ml) and adjusted to pH 9 by addition of triethylamine. The resulting deprotected dipeptide is added to a mixture of benzyloxycarbonylglycine (0.14 g, 0.67 mmol), 1-hydroxybenztriazole (0.103 g, 0.67 mmol) and N, N'-dicyclohexylcarbodi-imide (0.15 g, 0.7 mmol) in DMF (5 ml) which has been allowed to stand at 0° for 1 hour and at ambient for 1 hour. The mixture is set aside at ambient overnight, filtered and evaporated to an oil which is dissolved in dichloromethane (15 ml), extracted with 1M sodium bicarbonate (2×15 ml) followed by water (15 ml) and then dried (anhydrous magnesium sulphate). Evaporation affords a residue which is dissolved in ethyl acetate (25 ml) and extracted with citric acid (5×15 ml). The combined citric acid extracts are neutralised with solid sodium bicarbonate and extracted with ethyl acetate (5×15 ml). The ethyl acetate extracts are combined, dried (anhydrous magnesium sulphate) and evaporated to ca. 2 ml. The solution is set aside at 4° overnight to crystallise and the crystalline tripeptide (0.47 g, 74.5%) is collected: m.p. 146°, $[\alpha]_D^{20} - 15.78°$ (c 0.46 in MeOH). Amino acid analysis Gly 0.98, His 1.00, Phe 0.95.

Glycyl-L-histidyl-L-phenylalanine

A solution of the protected tripeptide (0.12 g, 0.15 mmol) in 80% acetic acid (5 ml) is hydrogenated at atmospheric pressure in the presence of palladium on carbon catalyst (0.02 g, 10% Pd). After 8 hours the reaction mixture is filtered and passed through a column of Amberlite IR45 ion-exchange resin (acetate form) to remove hydrogen bromide. The crude product is passed through a Sephadex G10 column twice to remove salts and in each case the Pauly positive fractions are pooled. The purified peptide is triturated with methanol to give a solid (49 mgs. 63%): m.p. 248°, $[\alpha]_D^{20} - 1.0°$ (c 1.0 in 1M acetic acid). Amino acid analysis Gly 0.98, His 1.00, Phe 0.95.

EXAMPLE 13

SOLID PHASE SYNTHESIS OF GLYCYL-L-HISTIDYL-L-PHENYLALANINE t-Butyloxycarbonyl-L-phenylalanyl resin A solution of t-butyloxycarbonyl-L-phenylalanine (2.64 g, 10 mmol) in methanol: water (45:5) is treated with aqueous cesium carbonate (20% W/V) until the pH of the solution is 7.0. The solution is evaporated to dryness, then re-evaporated from DMF (2×25 ml). The residue is dissolved in DMF (60 ml) and added to Merrifield 1% crosslinked polystyrene resin (8.6 g, 1.16 mequ.Cl/g). The mixture is allowed to stand at 60° for 16 hours and the resin is then collected by filtration, washed with DMF (3×100 ml), ethanol (3×100 ml) and dichloromethane (3×100 ml). The resultant t-butyloxycarbonyl-L-phenylalanyl resin is dried at ambient in vacuo and stored at 0°. Microanalysis gives N 1.15%. The nitrogen value indicates that the resin contains 0.82 mmol/g t-butyloxycarbonyl-L-phenylalanine.

Glycyl-L-histidyl-L-phenylalanine

The synthesis is carried out in a glass vessel. The resin is agitated by passing a stream of nitrogen gas upwards through a glass sinter. Peptide synthesis is carried out by a manual procedure. One cycle of the synthesis consists of the following operations (all solvent volumes 5 ml):

(a) dichloromethane 3×2 min.
(b) isopropanol 3×2 min.
(c) dichloromethane 3×2 min.
(d) trifluoroacetic acid in dichloromethane (40% v/v) 1×1 min.
(e) trifluoroacetic acid in dichloromethane (40% v/v) 1×30 min.
(f) dichloromethane 3×2 min.
(g) isopropanol 3×2 min.
(h) dichloromethane 3×2 min. Repeat (d), (e), f), (g), (h) then
(i) triethylamine in dichloromethane (10% v/v) 2×2 min.
(j) dichloromethane 5×2 min.
(k) coupling with 4 equ. t-butyloxycarbonyl amino acid and 4.4 equ. N, N'-dicylcohexylcarbodiimide in dichloromethane (5 ml) (1) DMF 3×2 min.

t-Butyloxycarbonyl-L-phenylalanyl resin (0.5 g, 0.4 mmol) is added to the synthesis vessel and the cycle is commenced at operation (a). In the first cycle N(α)-t-butyloxycarbonyl-N(π)-4-bromobenzyloxymethyl-L-histidine (0.736 g, 1.6 mmol) is used with N, N'-dicyclohexylcarbodiimide (0.37 g, 1.8 mmol).

In the second cycle, t-butyloxycarbonylglycine 0.28 g, 1.6 mmol) is used with N, N'-dicyclohexylcarbodiimide (0.37 g, 1.8 mmol). At the end of the second cycle the resin is washed with trifluoroacetic acid (2×5 min.) and suspended in trifluoroacetic acid (10 ml). A stream of hydrogen bromide gas is passed slowly through the suspension for 1.5 hours and the filtrate is collected and evaporated to dryness. The residue is washed with ether (3×20 ml), which is removed by decantation to leave a pale yellow solid. A solution of the solid in 25% acetic acid (5 ml) is passed through a column of Amberlite IR45 ion-exchange resin (acetate form) to remove hydrogen bromide and trifluoroacetic acid. The solution is applied to a Sephadex G10 column and eluted with 25% acetic acid. The Pauly positive fractions are pooled and evaporated to a glassy solid (0.091 g, 55%) which is indistinguishable from the glycyl-L-histidyl-L-phenylalanine made in Example 12, m.p. 249°, $[\alpha]_D^{20} - 1.0°$ (c 1.0 in 1M acetic acid). Amino acid analysis Gly 1.00, His 0.95, Phe 0.99.

EXAMPLE 14

Solid phase synthesis of 5-isoleucine angiotensin II

N(α)-t-Butyloxycarbonyl-L-phenylalanyl resin prepared as in Example 13, (0.42 g) is placed in a glass vessel and agitated by passing nitrogen gas upwards through a glass sinter. Peptide synthesis is carried out using a manual procedure, each cycle of the synthesis comprising treatment of the resin with (all solvent volumes 5 ml): (a) dichloromethane 3×2 min.; (b) isopropanol 3×2 min.; (c) dichloromethane 3×2 min.; (d) trifluoroacetic acid in dichloromethane (40% v/v) 1×1 min.; (e) trifluoroacetic acid in dichloromethane (40% v/v) 1×30 min.; (f) dichloromethane 3×2 min.; (g) isopropanol 3×2 min.; (h) dichloromethane 3×2 min.; repeat (d)–(h); (i) triethylamine in dichloromethane 3×2 min.; (j) dichloromethane 5×2 min.; (k) coupling with 4 equivalents of t-butyloxycarbonylamino acid and 4.4 equivalents of dicyclohexylcarbodiimide in dichloromethane (5 ml) except in the case of N(α)-t-butyloxycarbonyl, N(ω)-nitroarginine when dimethylformamide (5 ml) is used coupling is performed once for 4 h, then once for 16 h (except in the case of N(α)-t-butyloxycarbonyl, N(π)-benzyloxymethyl-L-histidine which is coupled once only for 4 h). Half of the final protected peptide-resin conjugate is washed with trifluoroacetic acid (10 ml) and then suspended in trifluoroacetic acid (5 ml) containing methoxybenzene (1 ml). A stream of hydrogen bromide gas is passed for 1h. Filtration and evaporation gives crude partially protected peptide hydrobromide which is triturated with ether, dissolved in 25% aqueous acetic acid, and passed several times through a column of Amberlite IR45 acetate form ion exchange resin, eluting with 25% aqueous acetic acid. Evaporation gives a hygroscopic solid which is dissolved in 80% aqueous acetic acid (10 ml). The solution is hydrogenated for 24 h in the presence of 10% palladium on carbon (50 mg) after which t.l.c. reveals only one major component. The solvent is removed and the oily residue (180 mg) is dissolved in 25% aqueous acetic acid and fractionated on a Sephadex G25 gel column swollen and eluted with 25% aqueous acetic acid. The Pauly-active fractions are combined and the gel filtration is repeated twice. T.l.c. still shows trace impurities so the peptide is dissolved in 0.0185M trimethylammonium acetate buffered to pH 4.2 and applied to a Whatman CM52 carboxymethyl cellulose cation exchange column (0.9×30 cm) and eluted with a linear pH and concentration gradient of 0.0185 pH 4.2 to 0.185 M pH 5.2 trimethylammonium acetate. The major Pauly active component is collected and the aqueous buffer is evaporated. The residue is repeatedly evaporated from water and finally dried in vacuo to give 5-*isoleucine angiotensin II* as a hygroscopic white solid (80 mg, 34%) which is indistinguishable from an authentic sample by t.l.c. in several systems or by 300 MNz n.m.r. spectroscopy. The specific rotation is $[\alpha]_D^{20} -65.5°$ (c 0.5, MHCl), calculated using concentration values for the monoacetate determined by amino acid analysis after hydrolysis of the solution in the presence of an internal standard: lit K Arakawa and F M Bumpus, *J. Amer Chem Soc* 1961, 83, 728 $[\alpha]_D^{20} -67°$ (c 0.4 M HCl) for the monoacetate. Amino acid analysis: Asp. 1.06; Arg. 1.01; Val. 1.01; tyr. 1.00; Ileu 0.99; His. 1.00; Pro. 0.99; Phe. 1.06.

EXAMPLE 15

GLYCYL-L-HISTIDYL-L-PHENYLALANINE
N($\alpha$)-t-Butyloxycarbonyl,
N($\pi$)-benzyloxymethyl-L-histidyl-L-phenylalanine methyl ester A mixture of N($\alpha$)-t-butyloxycarbonyl, N($\pi$)-benzyloxymethyl-L-histidine (0.375 g, 1.0 mmol), 1-hydroxybenzotriazole (0.168 g, 1.1 mmol) and N, N'-dicyclohexylcarbodiimide (0.248 g, 1.2 mmol) in DMF (5 ml) is set aside at 0° for 1 hour and then at ambient for 1 hour. To this is added a solution of L-phenylalanine methyl ester hydrochloride (0.237 g, 1.1 mmol) and triethylamine (0.167 ml, 1.2 mmol) in DMF (3 ml). The mixture is allowed to stand at ambient overnight, filtered and evaporated to a gum which is dissolved in ethyl acetate (20 ml). The ethyl acetate solution is extracted with 1 M sodium bicarbonate (2×15 ml), water (15 ml) and citric acid (5×15 ml). The combined citric acid extracts are neutralised (solid sodium bicarbonate) and extracted with ethyl acetate (5×15 ml). The ethyl acetate extracts are combined, dried (anhydrous magnesium sulphate) and evaporated to an oil which is dissolved in ether (15 ml) and evaporated to give a crisp foam (0.41 g, 81%): m.p. 45°–47°, $[\alpha]_D^{20} -10.4°$ (c 0.53 in MeOH).

t-Butyloxycarbonyl-glycyl-N($\pi$)-benzyloxymethyl-L-histidyl-L-phenylalanine methyl ester Solution I: A solution of t-butyloxycarbonyl-glycine (0.123 g, 0.7 mmol), 1-hydroxybenzotriazole (0.107 g, 0.7 mmol) and N, N'-dicyclohexylcarbodiimide (0.144 g, 0.7 mmol) in DMF (5 ml) is set aside at 0° for 1 hour then at ambient for 1 hour.

Solution II: Solution of the t-butyloxycarbonyl dipeptide methyl ester (0.3 g, 0.595 mmol) in trifluoroacetic acid (5 ml) is allowed to stand at ambient for 0.5 hours. Evaporation gives a residue which is washed with ether (3×15 ml). The ether is removed by decantation and the residue is dissolved in DMF (3 ml) and treated with triethylamine until the pH of the solution is 9.0.

Solution II is added to solution I and the mixture is set aside at ambient overnight. The filtered mixture is evaporated to an oil which is dissolved in ethyl acetate (25 ml). The ethyl acetate solution is extracted with 1M sodium bicarbonate (2×15 ml), water (15 ml) and citric acid (5×15 ml). The combined citric acid extracts are neutralised (solid sodium bicarbonate) and extracted with ethyl acetate (5×15 ml). The ethyl acetate extracts are combined, dried (anhydrous magnesium sulphate) and evaporated to an oil. A solution of the oil in ether (10 ml) is evaporated to a crisp foam (0.30 g, 85%): $[\alpha]_D^{20} -13.95°$ (c 0.49 in MeOH).

Glycyl-L-histidyl-L-phenylalanine

The protected tripeptide (0.10 g, 0.169 mmol) is saponified at ambient in a mixture of methanol (1 ml) and 1M sodium hydroxide (0.186 ml, 0.186 mmol). After 1 hour the solution is diluted with (25 ml), acidified to pH 4 with 1M hydrochloric acid and extracted with dichloromethane (5×15 ml). The combined dichloromethane extracts are dried (anhydrous magnesium sulphate) and evaporated to a solid residue. A solution of the residue in 80% acetic acid (10 ml) is hydrogenated at atmospheric pressure in the presence of palladium on carbon catalyst (20 mgs, 10% Pd). After 4 hours the filtered solution is evaporated to a solid residue. The residue is dissolved in trifluoroacetic acid (5 ml), set aside at ambient for 0.5 hours and evaporated. A solution of the residue in 25% acetic acid (3 ml) is passed through a column of Amberlite IR45 ion-exchange resin (acetate form) to remove trifluoroacetic acid and then applied to a column of Sephadex G10. The column is eluted with 25% acetic acid and the Pauly positive fractions are pooled and evaporated to an oil which is co-evaporated with water (3×10 ml) to give a white solid which is indistinguishable from the glycyl-L-histidyl-L-phenylalanine prepared in Example 12 (0.045 g, 67.5%).

EXAMPLE 16

N($\alpha$)-t-Butyloxycarbonyl,N($\pi$)-benzyloxymethyl-L-histidyl-L-tryptophan methyl ester 1-Hydroxybenzotriazole (243 mg. 1.60 mmol) and N, N'-dicyclohexylcarbodiimide (328 mg, 1.60 mmol) are added to a solution of N($\alpha$)-t-butyloxycarbonyl,N($\pi$)-benzyloxymethyl-L-histidine (500 mg, 1.33 mmol) and L-tryptophan methyl ester (339 mg, 1.40 mmol) in a mixture of dimethylformamide (2 ml) and chloroform (8 ml) stirred at 0° which has just previously been adjusted to pH 9 by the addition of triethylamine. After 1h at 0° the mixture is allowed to attain room temperature overnight. Filtration and evaporation of the solvent gives a yellow oil which is dissolved in chloroform (10 ml) and cooled to 0° for 1h after which a second crop of dicyclohexylurea is removed by filtration. The filtrate is diluted with chloroform (10 ml) and washed with saturated sodium hydrogen carbonate (2×10 ml) before extraction with 10% citric acid (4×20 ml). The citric acid extracts are combined and adjusted to pH 8.5 by the addition of solid sodium hydrogen carbonate before extraction with chloroform (4×50 ml). The combined organic extracts are dried and evaporated to give, after trituration with ether, a white solid. Crystallisation from methanol-ether gives N($\alpha$)-t-butyloxycarbonyl,N($\pi$)-benzyloxy methyl-L-histidyl-L-tryptophan methyl ester (476 mg, 61%) of m.p. 90°14 92°, $[\alpha]_D^{20}$ +3.1° (c 1.0, MeOH).

N($\alpha$)-t-Butyloxycarbonyl-L-histidyl-L-tryptophan methyl ester

The preceding protected dipeptide (100 mg, 0.17 mmol) is dissolved in 80% aqueous acetic acid (5 ml). Palladium on carbon (5%, 30 mg) is added and the suspension is hydrogenated for 2h after which t.l.c. indicates that all the starting material has been consumed. Filtration and evaporation gives, after trituration with ether, N(α)-t-butyloxycarbonyl-L-histidyl-L-tryptophan methyl ester as a white solid (58 mg, 73%) of m.p. 164°-165° [α]$_D^{20}$ −3.7° (c 1.0, MeOH).

EXAMPLE 17

N(α)-t-butyloxycarbonyl,N(π)-benzyloxymethyl-L-histidyl-N(π)-benzyloxymethyl-L-histidine methyl ester -

A solution of N(α)-t-butyloxycarbonyl, N(π)-benzyloxymethyl-L-histidine methyl ester hydrochloride (1.0 g, 2.35 mmol) in trifluoroacetic acid (10 ml) is allowed to stand for 0.5h. The solvent is then evaporated and the residue is treated with ether (50 ml). After 1h at 4° the ether is decanted and fresh ether (50 ml) is added. The mixture is allowed to stand at 4° overnight, after which the ether is removed by decantation. The oily residue is dissolved in dimethylformamide (3 ml) and the pH is adjusted to 9 by the addition of triethylamine. This solution is immediately added to an ice-cooled solution of N,N'-dicyclohexylcarbodiimide (0.59 g, 2.85 mmol), 1-hydroxybenzotriazole (0.4 g, 2.6 mmol) and N(α)-t-butyloxycarbonyl,N(π)-benzyloxymethyl-L-histidine (0.98 g, 2.6 mmol) in dimethylformamide (5 ml). The solution is set aside overnight, filtered and evaporated to give a solid which is suspended in dichloromethane (30 ml), extracted with 10% sodium carbonate (15 ml) dried and evaporated to give an oil which is dissolved in ethyl acetate (5 ml) and allowed to stand at 4° overnight. Further dicyclohexylurea is then removed by filtration and the solution is evaporated to give an oil. Flash chromatography on a column of silica gel eluted wth chloroform-methanol (9:1) gives fully protected dihistidine (1.05 g, 67%) as a powder of m.p. 54°-59° [α]$_D^{20}$ −12.1° (c 1.2, MeOH).

L-Histidyl-L-histidine-

M Sodium hydroxide (0.56 ml, 0.56 mmol) is added to a solution of the preceding protected dipeptide (0.3 g, 0.45 mmol) in methanol (1 ml). Water (50 ml) is added after 15 min. and the pH is adjusted to 4.5 by the dropwise addition of M hydrochloric acid. The solution is extracted with ethyl acetate (6×15 ml) and the combined ethyl acetate extracts are dried and evaporated. A solution of the residue in 80% aqueous acetic acid (20 ml) is hydrogenated overnight in the presence of 10% palladium on carbon (50 mg). Filtration and evaporation gives an oily residue which is dissolved in trifluoroacetic acid (5 ml) and set aside for 0.5h. The solvent is evaporated and the residue is treated with ether (3×50 ml) which is removed by decantation. The residue is dissolved in 25% aqueous acetic acid (2 ml) and passed through a column of Amberlite IR45 anion exchange resin (acetate form). Chromatography on a column of Sephadex G25 swollen and eluted with 25% aqueous acetic acid and collection of the Pauly-active fractions gives after drying at 0.1 mm overnight dihistidine (66 mg, 38%) as a hygroscopic powder of indefinite m.p., [α]$_D^{20}$ −8.7° (c 0.5, M AcOH). N(α)-t-Butyloxycarbonyl,N(π)-benzyloxymethyl-L-histidyl-N(π)benzyl oxymethyl-L-histidyl-N(π)-benzyloxymethyl-L-histidine methyl ester- Solution A: a solution of the preceding protected dipeptide (0.774 g, 1.2 mmol) intrifluoroacetic acid (10 ml) is allowed to stand for 0.5h; the solvent is evaporated and the residue is treated with ether (50 ml); after 1h at 4° the ether is decanted and replaced with fresh ether (50 ml); the mixture is set aside at 4° overnight and the ether is removed by decantation; the residue is dissolved in dimethylformamide (5 ml).

Solution B: a solution of N(α)-t-butyloxycarbonyl,N(π)-benzyloxymethyl-L-histidine (0.45 g, 1.2 mmol) N,N'-dicyclohexylcarbodiimide (0.272 g, 1.32 mmol) and 1-hydroxybenzotriazole (0.184 g, 1.2 mmol) in dimethylformamide (5 ml) is stirred at 0° for 0.5h and then at room temperature for 0.5h.

The pH of solution A is adjusted to 9 by the addition of triethylamine and it is immediately added to solution B. The resultant solution is set aside overnight. Filtration and evaporation gives an oil which is dissolved in ethyl acetate (10 ml) and set aside at 4° overnight. Further dicyclohexylurea is removed by filtration and the solution is evaporated. A solution of the residue in dichloromethane (40 ml) is washed with 10% sodium carbonate, dried and evaporated giving fully protected trihistidine (0.79 g, 63%) as a crisp meringue: m.p. 58°-64°[α]$_D^{20}$ −27.6° (c0.5, MeOH).

L-Histidyl-L-histidyl-L-histidine -

Sodium hydroxide (M, 0.6 ml) is added to a solution of the preceding fully protected tripeptide (0.5 g, 0.54 mmol) in methanol (2 ml). The solution is stirred for 15 min and then water (50 ml) is added and the pH is adjusted to 4.5 by the dropwise addition of M hydrochloric acid. The solution is extracted with ethyl acetate (6×15 ml) and the combined ethyl acetate extracts are dried and evaporated. A solution of the residue in 80% aqueous acetic acid (20 ml) is hydrogenated overnight in the presence of 10% palladium on carbon (50 mg). The residue after filtration and evaporation is dissolved in trifluoroacetic acid (5 ml). After 0.5h the trifluoroacetic acid is evaporated and the resulting oil is treated with ether (3×50 ml) which is removed by decantation. The residue is dissolved in 25% acetic acid (2 ml) and passed through a column of Amberlite IR45 anion exchange resin (acetate form). T.l.c. at this stage shows the presence of 2 major components in approximately equal amounts. The hydrogenation procedure is repeated for 2h which suffices to complete the reaction. Fractionation on a column of Sephadex G25 swollen and eluted with 25% aqueous acetic acid and combination of the principal Pauly-active fractions, evaporation and overnight drying at 0.1 mm gives trihistidine (146 mg, 42%) as a powder of m.p. 107°-115°,[α]$_D^{20}$ +11.9° (c 1.0, M AcOH).

What is claimed is:

1. A compound of formula I

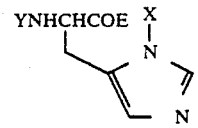

wherein X is —CH$_2$OCH$_2$Ar in which Ar represents phenyl or p-bromophenyl, Y represents Boc, Fmoc or, benzyloxycarbonyl, or hydrogen, and E represents OH or OR, wherein R is a C$_1$-C$_6$ alkyl group.

2. A compound of formula I

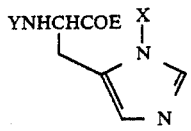

wherein X is —CH₂OCH₂Ar in which Ar represents phenyl or p-bromophenyl, Y represents Boc, Fmoc or benzyloxycarbonyl, and E represents OH.

3. The compound of claim 1, wherein Ar is phenyl.
4. The compound of claim 2, wherein Ar is phenyl.
5. The compound of claim 1, wherein Ar is p-bromophenyl.
6. The compound of claim 2, wherein Ar is p-bromophenyl.
7. The compound of claim 1, wherein Y is Boc.
8. The compound of claim 1, wherein Y is Fmoc.
9. The compound of claim 1, wherein Y is benzyloxycarbonyl.
10. The compound of claim 1, wherein Y is hydrogen.
11. The compound of claim 2, wherein Y is Boc.
12. The compound of claim 2, wherein Y is Fmoc.
13. The compound of claim 2, wherein Y is benzyloxycarbonyl.
14. The compound of claim 1, wherein E is OH.
15. The compound of claim 1, wherein E is OR.

* * * * *

UNITED STATES PATENT AND TRADEMARK OFFICE
CERTIFICATE OF CORRECTION

PATENT NO. : 4,591,648

DATED : MAY 27, 1986

INVENTOR(S) : JONES et al.

It is certified that error appears in the above-identified patent and that said Letters Patent is hereby corrected as shown below:

Column 1, line 46, last word, for "an" read --a--.

Column 4, line 4, for "4°; m.p." read --4°: m.p.--.

Column 4, line 28, for "Example 1; m.p." read

--Example 1: m.p.--.

Column 4, line 34, for "5.9 mmol)" read --5.9 mmol--.

Column 6, line 34, after "dried (" insert --anhydrous--.

Column 6, beginning of line 63, after "(", insert

--anhydrous--.

Column 7, line 12, end of line, before the numeral "4"

delete "(".

Column 7, line 13, delete ")".

Column 7, line 14, for "0.075 g, 0.05" read --0.075 g, 0.5--.

Column 7, line 15, for "0.071 ml, 0.05 mmol" read --0.071 ml, 0.5 mmol--.

UNITED STATES PATENT AND TRADEMARK OFFICE
CERTIFICATE OF CORRECTION

PATENT NO. : 4,591,648                                    Page 2 of 3
DATED      : MAY 27, 1986
INVENTOR(S): JONES et al.

It is certified that error appears in the above-identified patent and that said Letters Patent is hereby corrected as shown below:

Column 8, line 12, for "N'-dicyclohexylcarbodiimide"

read --N'-dicyclohexylcarbodi-imide--.

Column 8, line 37, seventh word, for "state" read --stage--.

Column 9, line 15, for "(49 mgs. 63%)" read --(49 mgs, 63%)--.

Column 9, line 63, for "N'dicylohexylcarbodiimide"

read --N'dicyclohexylcarbodi-imide--.

Column 9, line 64, for "(5ml)(1)" read --(5ml).(1)--.

Column 10, line 3, for "0.28" read --(0.28--.

Column 10, line 52, after "passed for", for "1h."

read --1 h.--.

Column 10, lines 56-57, for

"ion exchange" read --ion-exchange--.

Column 11, line 11, for "300 MNz" read --300 MHz--.

Column 11, line 13, for "MHCl" read --M HCl--.

UNITED STATES PATENT AND TRADEMARK OFFICE
CERTIFICATE OF CORRECTION

PATENT NO. : 4,591,648
DATED : MAY 27, 1986
INVENTOR(S) : JONES et al.

It is certified that error appears in the above-identified patent and that said Letters Patent is hereby corrected as shown below:

Column 11, line 19, for "Ileu 0.99;" read --Ileu. 0.99;--.

Column 11, beginning of line 55, for "Solution II:Solution" read --Solution II: A solution--.

Column 12, line 36, for "243 mg." read --243 mg,--.

Column 12, line 59, for "m.p. 90°14 92°" read --m.p. 90° - 92°--.

Column 14, line 20, for "(0.79g, 63%)", read --(0.70g, 63%)--.

Column 14, line 28, first word, for "min" read --min.--.

Signed and Sealed this

Seventeenth Day of March, 1987

Attest:

DONALD J. QUIGG

Attesting Officer

Commissioner of Patents and Trademarks